(12) United States Patent
Tegg et al.

(10) Patent No.: US 12,144,532 B2
(45) Date of Patent: Nov. 19, 2024

(54) APPARATUS AND SYSTEM FOR CRYO-THERAPY BALLOON

(71) Applicant: St. Jude Medical, Cardiology Division, Inc., St. Paul, MN (US)

(72) Inventors: Troy T. Tegg, Elk River, MN (US); Salo Arias, Brooklyn Park, MN (US); Derek C. Sutermeister, Ham Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 449 days.

(21) Appl. No.: 16/758,789

(22) PCT Filed: Oct. 26, 2018

(86) PCT No.: PCT/US2018/057762
§ 371 (c)(1),
(2) Date: Apr. 23, 2020

(87) PCT Pub. No.: WO2019/084439
PCT Pub. Date: May 2, 2019

(65) Prior Publication Data
US 2021/0177482 A1    Jun. 17, 2021

Related U.S. Application Data

(60) Provisional application No. 62/578,201, filed on Oct. 27, 2017.

(51) Int. Cl.
*A61B 18/02* (2006.01)
*A61B 18/00* (2006.01)

(52) U.S. Cl.
CPC .... *A61B 18/02* (2013.01); *A61B 2018/00255* (2013.01); *A61B 2018/00375* (2013.01);
(Continued)

(58) Field of Classification Search
CPC .......................... A61B 18/02; A61B 18/1206
See application file for complete search history.

(56) References Cited

U.S. PATENT DOCUMENTS 6,235,019 B1   5/2001  Lehmann et al.
8,052,680 B2  11/2011  Hassett et al.
(Continued)

FOREIGN PATENT DOCUMENTS

EP      3120792 A1   1/2017
WO   2019083765 A1   5/2019
WO   2019084442 A1   5/2019

*Primary Examiner* — Daniel W Fowler
(74) *Attorney, Agent, or Firm* — Armstrong Teasdale LLP

(57) ABSTRACT

Various embodiments of the present disclosure can include a medical device for providing therapy to heart tissue. The medical device can comprise a balloon, a movable manifold, wherein the movable manifold comprises a first plurality of openings and the movable manifold is inside the balloon and the movable manifold is configured to distribute a fluid within the balloon, an elongate shaft with a proximal end portion and a distal end portion, wherein the distal end portion of the elongate shaft is coupled with the balloon, a central lumen, wherein the movable manifold is movably coupled with the central lumen, and a supply lumen comprising a supply lumen proximal end and a supply lumen distal end, wherein the supply lumen is longitudinally movable and in fluid communication with the movable manifold, wherein the movable manifold is configured to move longitudinally in response to an actuation of the supply lumen proximal end.

18 Claims, 5 Drawing Sheets

(52) U.S. Cl.
CPC ............... *A61B 2018/00577* (2013.01); *A61B 2018/00744* (2013.01); *A61B 2018/0212* (2013.01); *A61B 2018/0262* (2013.01); *A61B 2218/002* (2013.01); *A61B 2218/007* (2013.01)

(56) References Cited

U.S. PATENT DOCUMENTS

| | | | |
|---|---|---|---|
| 2009/0118723 A1* | 5/2009 | Lalonde | A61B 18/02 606/22 |
| 2009/0234345 A1 | 9/2009 | Hon | |
| 2009/0299356 A1* | 12/2009 | Watson | A61M 25/1011 606/21 |
| 2010/0305562 A1* | 12/2010 | Winkler | A61B 18/1482 606/41 |
| 2011/0184398 A1* | 7/2011 | Desrochers | A61M 25/1011 606/21 |
| 2012/0101485 A1* | 4/2012 | Wittenberger | A61M 25/0147 606/21 |
| 2013/0030425 A1* | 1/2013 | Stewart | A61B 18/02 606/41 |
| 2013/0110099 A1* | 5/2013 | Groves | A61M 25/007 606/21 |
| 2013/0197499 A1* | 8/2013 | Lalonde | A61B 18/02 606/21 |
| 2014/0046252 A1 | 2/2014 | Boatman et al. | |
| 2015/0119868 A1* | 4/2015 | Lalonde | A61B 18/14 606/21 |
| 2015/0265329 A1 | 9/2015 | Lalonde et al. | |
| 2017/0042449 A1 | 2/2017 | Deno et al. | |
| 2017/0119468 A1* | 5/2017 | Richmond | A61B 90/30 |
| 2019/0357959 A1 | 11/2019 | Hou et al. | |
| 2020/0085483 A1 | 3/2020 | Olson et al. | |
| 2020/0085484 A1 | 3/2020 | Tegg et al. | |

* cited by examiner

APPARATUS AND SYSTEM FOR CRYO-THERAPY BALLOON

CROSS-REFERENCE TO RELATED APPLICATIONS

This application is a U.S. National Stage Entry of International Application No. PCT/US2018/057762, filed Oct. 26, 2018, which claims the benefit of U.S. provisional application No. 62/578,201, filed Oct. 27, 2017, which are hereby incorporated by reference as though fully set forth herein.

BACKGROUND a. Field

This disclosure relates to an elongate medical device. In particular, the instant disclosure relates to apparatuses and systems for cryo-therapy balloons.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

In the case of an ablation balloon filled with a fluid/gas, various tissue adjacent the balloon can be ablated to create lesions. In the case of ablation balloons used for cryo-therapy in and proximate a PV, controlling the flow direction of the fluid in the balloon is important for targeting specific tissue adjacent the balloon and avoiding undesired treatment of other tissue adjacent the balloon.

BRIEF SUMMARY

The instant disclosure, in at least one embodiment, an medical device for providing therapy to tissue, comprises a balloon, a movable manifold, wherein the movable manifold comprises a first plurality of openings and the movable manifold is inside the balloon and the movable manifold is configured to distribute a fluid within the balloon, an elongate shaft with a proximal end portion and a distal end portion, wherein the distal end portion of the elongate shaft is coupled with the balloon, a central lumen, wherein the movable manifold is movably coupled with the central lumen, and a supply lumen comprising a supply lumen proximal end and a supply lumen distal end, wherein the supply lumen is longitudinally movable and in fluid communication with the movable manifold, wherein the movable manifold is configured to move longitudinally in response to an actuation of the supply lumen proximal end.

In another embodiment, a medical therapy apparatus comprises a balloon, positioned at a distal end portion of an elongate structure, a central lumen coupled with the balloon, a manifold comprising a first port and a second port in fluid communication with an interior of the balloon, wherein the manifold is coupled with the central lumen, and a movable manifold cover, wherein the movable manifold cover can cover one or more of the first port and the second port and block the fluid communication between the central manifold and the interior of the balloon.

In yet another embodiment, a medical device comprises a balloon, positioned at a distal end portion of an elongate structure, a central lumen coupled with the balloon, a movable manifold comprising a distribution element, wherein the manifold is coupled with the central lumen, and a distribution control element movably coupled with the distribution element.

DETAILED DESCRIPTION OF EMBODIMENTS

The instant disclosure relates to catheters for providing an ablation therapy to tissue, and more specifically, ablation of myocardial tissue with electrophysiology catheters within the heart. In particular, the instant disclosure relates to a balloon that uses a fluid flowing through a movable manifold inside the balloon. The tissues, such as myocardial tissues including the pulmonary vein, can receive an ablation therapy from the fluid within the balloon to alleviate symptoms associated with cardiac arrhythmias. The tissue ablation can produce a consistent tissue ablation line along a length and circumference of the pulmonary venous tissue which substantially blocks the transmission of electrical signals between ectopic foci within the pulmonary vein (PV). Details of the various embodiments of the present disclosure are described below with specific reference to the figures.

Figure 1:
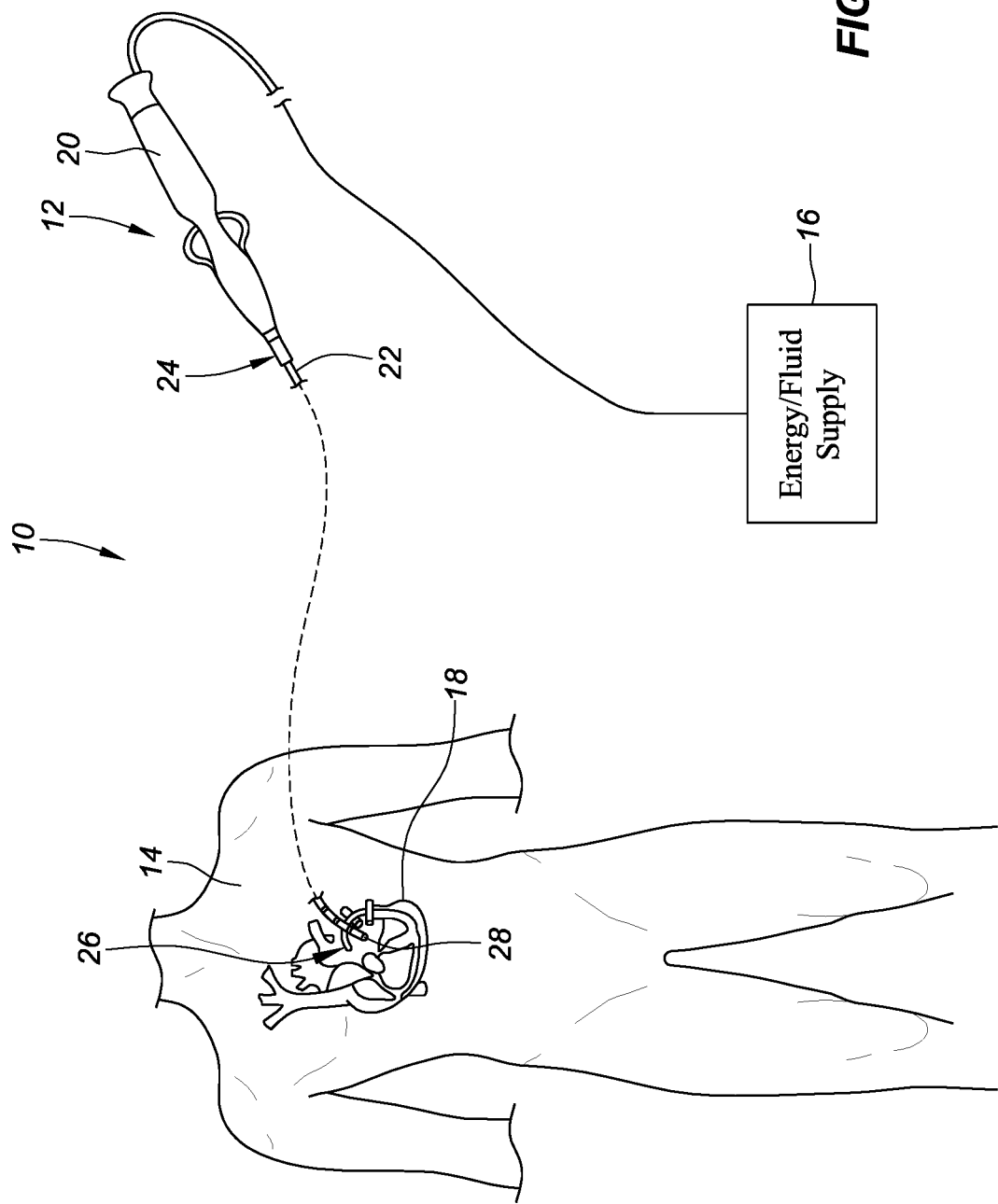
FIG. 1 is an exemplary system diagram of a catheter inserted into a body (the heart) with an irrigation system including an energy/fluid supply.

Referring now to the drawings wherein like reference numerals are used to identify similar components in the various views, FIG. 1 is a system diagram showing a medical device and an energy/fluid supply, in accordance with embodiments of the present disclosure. In some embodiments, and with reference to FIG. 1, the system 10 can include a medical device 12 and an energy/fluid supply 16 (e.g., an RF signal generator, a coolant supply, a pump, etc.). The energy/fluid supply 16 can also include an electronic control unit (ECU). In an embodiment, the catheter 12 may be an ablation catheter. The catheter 12 can be configured to be inserted into a patient's heart 18.

The catheter 12 may include a handle 20 and a shaft 22 having a proximal end portion 24, a distal end portion 26, and a tip portion 28 disposed at the distal end portion 26 of the shaft 22. The catheter 12 may further include other conventional components such as, for example and without limitation, a temperature sensor, a position sensor, a pressure sensor, and/or additional sensors or electrodes, and corresponding conductors or leads. For purposes of illustration and clarity, the description below will be limited to an embodiment wherein the medical device 12 comprises a catheter (a sample catheter is shown in FIG. 1 (e.g., catheter 12)). It will be appreciated, however, that the present disclosure is not meant to be limited to catheters The shaft 22 can be an elongate, tubular, flexible member configured for movement within the body 14. The tip portion 28 of the shaft 22 supports, for example and without limitation, sensors and/or electrodes mounted thereon. The tip portion 28 may include ablation elements (e.g., ablation tip electrodes for delivering RF energy to fluid in a balloon and/or for delivering RF ablative energy to tissue, cryo ablation using a focal tip, including a separate lumen extending to the focal tip). The shaft 22 may also permit transport, delivery, and/or removal of fluids (including irrigation fluids, cryogenic ablation fluids, and bodily fluids), medicines, and/or surgical tools or instruments.

Figure 2A:
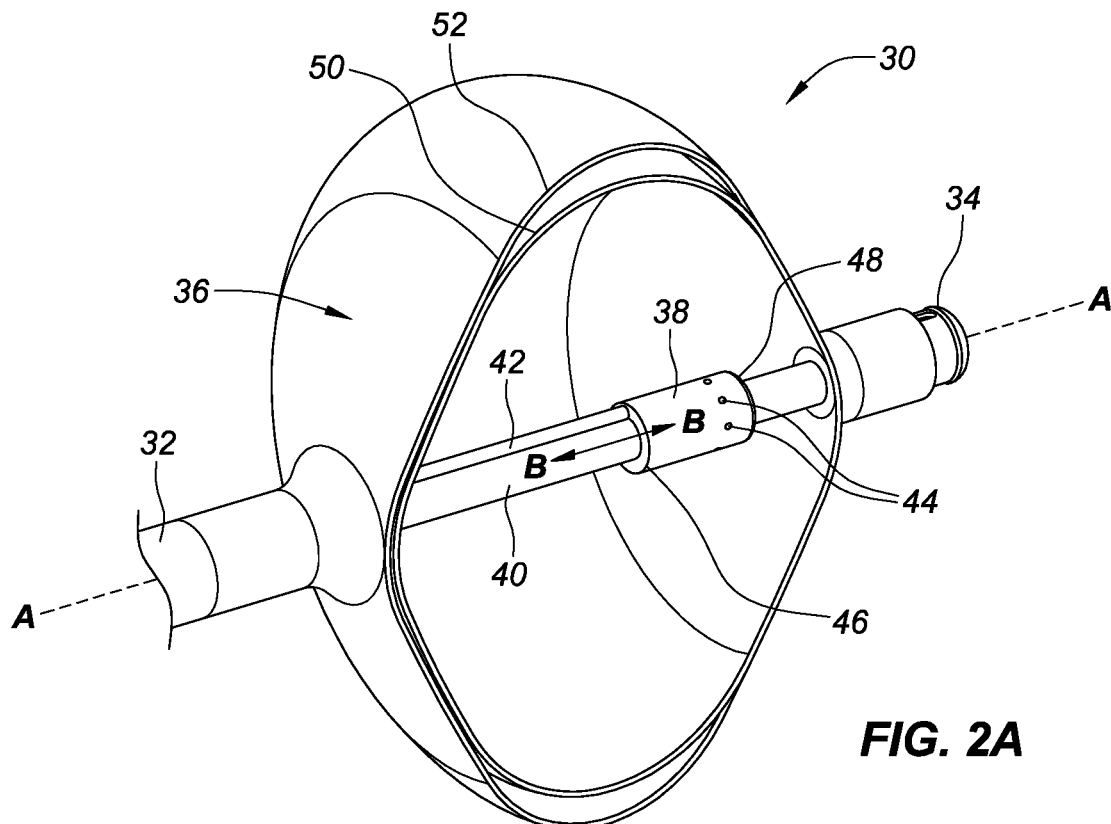
FIG. 2A is partial fragmentary view of a distal end of an elongate medical device coupled with a balloon with a movable manifold, consistent with embodiments in the present disclosure.

FIG. 2A is a partial fragmentary view of a distal end of an elongate medical device coupled with a balloon with a movable manifold, consistent with embodiments in the present disclosure. The balloon apparatus 30 can include a longitudinal axis defined by the line A-A, the elongate medical device 32 with a distal end 34 coupled to a balloon 36 and a movable manifold 38. The movable manifold 38 can be slideably coupled with a central lumen 40 of the elongate medical device 32 and within a portion of the balloon 36. The movable manifold 38 can be connected, for example, to a pump (e.g., a pump that is part of the energy/fluid supply 16 of FIG. 1) by a manifold supply lumen 42. The manifold supply lumen 42 can be internal and/or external to the central lumen 40 of the elongate medical device 32. The manifold supply lumen 42 can allow fluid or gas to flow through the movable lumen 38. For example, the fluid/gas can flow from the energy fluid supply 16 (FIG. 1), through the manifold supply lumen 42, through the movable manifold 38, and into the balloon 36). In some embodiments, the manifold supply lumen 42 can be divided to allow for greater control of dispersal of the fluid or gas to different portions of the movable manifold. (See FIG. 3 and related discussion for additional information).

The manifold supply lumen 42 can also be sufficiently rigid to be used to move the movable manifold 38 longitudinally as indicated by the arrow B-B. For example, the manifold supply lumen 42 can be coupled with the movable manifold 38 and a control interface can be used to move/translate the movable manifold 38 (e.g., a user can push/pull on the control interface that interacts with a proximal portion of the manifold supply lumen 42 that results in longitudinal movement of the movable manifold 38).

The movable manifold 38 can include any suitable number and configuration of openings 44 (e.g., orifices, nozzles, fittings and other similar elements) that facilitate a flow of the fluid or a gas from the manifold supply lumen 42 through the movable manifold 38 and into the balloon 36. A portion of the movable manifold can comprise a distribution element. As shown in FIG. 2A, the openings 44 can be arranged in a line around the circumference of the movable manifold 38 with equal spacing between the openings 44. In some embodiments (not shown), the openings 44 can have variable spacing between each opening. The movable manifold 38 can include a movable manifold proximal end 46 and a movable manifold distal end 48, with openings 44 proximate the movable manifold distal end 48.

The openings 44 can be distributed along the length of the movable manifold 38 with any suitable spacing. The openings 44 can also be spaced radially around the movable manifold 38. The openings 44 can be positioned to provide various patterns of discharge of the fluid/gas into the balloon 36. The openings 44 can be, for example, the same size or they can be different sizes or any suitable combination of sizes. The openings 44 can also provide directional control when the fluid/gas is discharged into the balloon 36. The movable manifold 38 can include openings 44 proximate the movable manifold distal end 48, proximate the movable manifold proximal end, inbetween those two locations, and/or any combination locations along the movable manifold 38. In some embodiments, the openings 44 can also include a nozzle on one or more of the openings (not shown). The nozzle can be used to control or direct the flow of the fluid/gas. For example, the nozzle can be configured to direct the fluid/gas to a specific location/area of the balloon 36 or to discharge the fluid/gas in a specific pattern.

The openings 44 can include, for example, groups of openings (not shown) at different locations along the length of the movable manifold 38. For example, a first group of openings can be spaced radially around a first location on movable manifold 38 and a second group of openings can be spaced radially around a second location on the movable manifold 38. Any suitable number of groups of openings 44 can be used and the number of openings 44 in each group can be the same or different. The sizes of the each of the openings 44 in the various groups can be the same or different.

Additional information about configurations for the openings and the supply of fluid can be found in U.S. application No. 62/457,666 filed on 10 Feb. 2017, which is hereby incorporated by reference as if set forth fully herein. The movable manifold 38 can be moved longitudinally (e.g., distally and/or proximally) within the balloon 36 in a direction indicated by the arrow B-B. The movable manifold 38 can be movably coupled with the central lumen 40 (e.g., the movable manifold 38 can slide along the central lumen 40). The longitudinal movement of the movable manifold 38 can be achieved by the use of various elements including, for example, the manifold supply lumen 42, activation and/or pull wires or other similar devices that mechanically couple the movable manifold 38 with a user control (e.g., a handle, etc.) or a combination of these elements.

An interior of the manifold 38 can be an expansion chamber. Additional information on embodiments of the manifold and the expansion chamber can be found in U.S. application 62/457,666, filed on 10 Feb. 2017, which is hereby incorporated by reference as if set forth fully herein.

The elongate medical device 32 can be an elongated, tubular, and flexible member configured for movement within a patient's body 14. The elongate medical device 32 can include the balloon 36 at a distal end 34. The balloon 36 and the elongate medical device can be combined into a single element or they can be separate elements that are coupled together. The elongate medical device 32 may also permit transport, delivery and/or removal of fluids (including irrigation fluids (e.g., saline), cryogenic ablation fluids/gasses, and body fluids), medicines, and/or surgical tools or instruments. The transport, delivery and/or removal of fluids can be done through, for example, the central lumen 40, the supply lumen 42, and/or other lumens. The elongate medical device 32, which may be made from conventional materials used for catheters, such as polyurethane, can include one or more lumens configured to house and/or transport electrical conductors, fluids, and/or surgical tools. The elongate medical device 32 may be introduced into a blood vessel or other structure within the body 14 through, for example, a conventional introducer sheath.

The balloon 36 can be either of a conductive or a nonconductive material and can be either self-erecting or mechanically erected, such as through the use of an internal balloon. In some embodiments, a balloon and an elongate medical device can combined into a single element (not shown). The balloon 36 can be made of any suitable material (e.g., flexible polymers such as nylon, polyamide (e.g., a polyether block amide such as PEBAX), polyurethane, polyethylene terephthalate (PET), etc.). The balloon 36 can be made from a material that is compliant (e.g., expands as internal pressure increases) or non-compliant/semi-compliant (e.g., expands to one specific size or size range, even as internal pressure increases). The balloon 36 can be any suitable shape (round, oval, elliptical, etc.) and can be symmetrical or asymmetrical.

The balloon 36 can include two layers (e.g., a first balloon 50 inside of a second balloon 52) as shown in FIG. 2A. In other embodiments (not shown), the balloon 36 can have one layer (e.g., where the layer is considered a single balloon), multiple layers where each layer can be considered a separate balloon (a third balloon, a fourth balloon, etc.), or multiple layers that are considered a single balloon. The various layers of the balloon 36 can be the same shape or they can be different shapes. Additional balloon shapes and configurations are described in U.S. application No. 62/432,065, filed on Dec. 9, 2016, and U.S. application No. 62/578,178, filed on Oct. 27, 2017, which are hereby incorporated by reference as if set forth fully herein.

In an exemplary embodiment, a lumen (e.g., the central lumen 40) extending through a length of a shaft (e.g., a shaft 22 of FIG. 1) of the elongate medical device 32 can inject a fluid (e.g., a fluid and/or a gas) into the balloon 36 which exerts a radial force on the balloon 36 and thereby expands the balloon 36 into a deployed/inflated (e.g., expanded) configuration. The balloon 36 can also be expanded using, for example, a mechanical structure (not shown) that includes a shape memory material (e.g., nitinol) and/or pull wires, activation wires, or other suitable method and hardware.

Figure 2B:
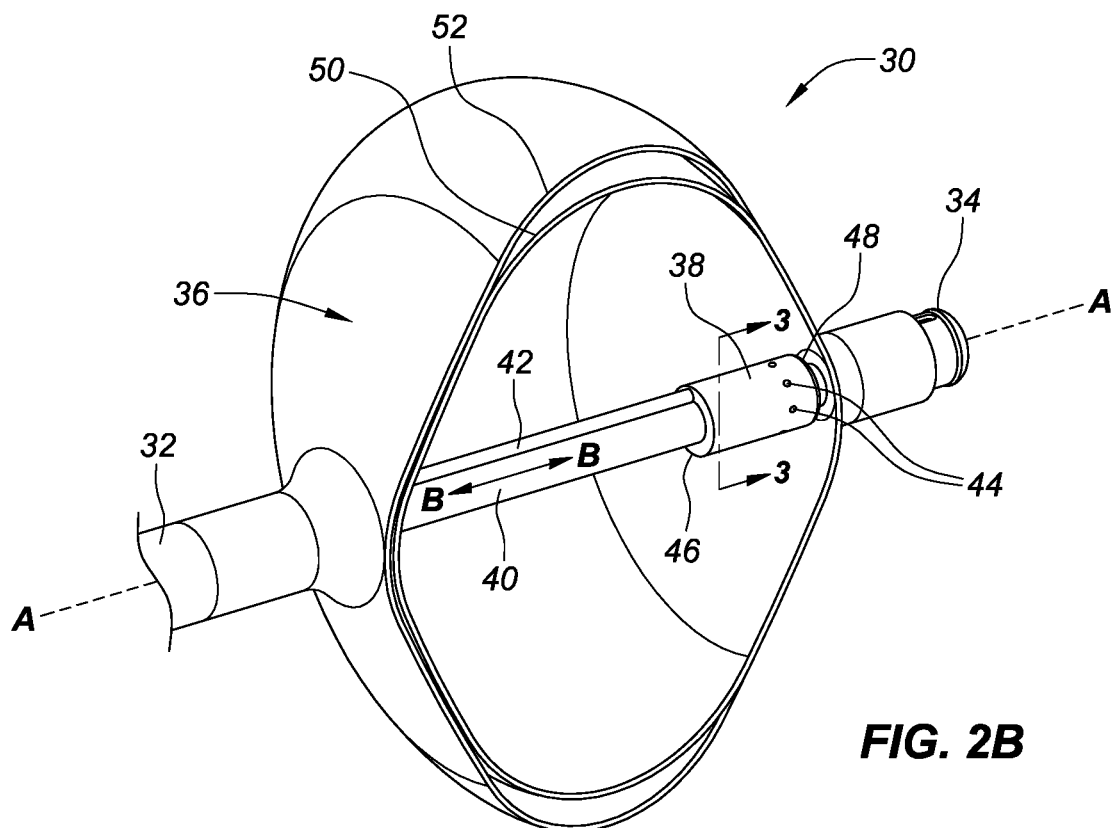
FIG. 2B is a partial fragmentary view of the distal end of the elongate medical device coupled with the balloon with the movable manifold of FIG. 2A, where the movable manifold is translated longitudinally, consistent with embodiments in the present disclosure.

FIG. 2B is a partial fragmentary view of the distal end of the elongate medical device with the balloon with the movable manifold of FIG. 2A, where the movable manifold is translated longitudinally, consistent with embodiments in the present disclosure. As described above, the balloon apparatus 30 can include the elongate medical device 32 with the distal end 34 coupled to the balloon 36 and the movable manifold 38 as shown in FIG. 2A. In FIG. 2B, the movable manifold 38 has been longitudinally translated distally (e.g., moved more distally as shown in FIG. 2B). Translation of the movable manifold 38 can allow for variations in the therapy permitted by the balloon apparatus 30. For example, translating the movable manifold 38 longitudinally can allow for a different flow pattern of the fluid/gas that is moving into the balloon 36. This variation in flow can permit, for example, targeting different portions of the balloon 36 with the fluid/gas flowing from the openings 44 of the movable manifold 38. This can lead to variations in treatment sites of tissue proximate the balloon 36 when the balloon is in contact with tissue (e.g., proximate a PV).

In the embodiment shown in FIGS. 2A-B, the balloon 36 and the elongate medical device 32 can be combined into a single element. In other embodiments, the balloon 36 can be coupled with the elongate medical device 32 where the balloon 36 and the elongate medical device 32 are separate elements (not shown). The balloon 36 can be made of any suitable material (e.g., flexible polymers such as nylon, PEBAX, polyurethane, PET, etc.). The balloon 36 can be any suitable shape (round, oval, elliptical, etc.) and can be symmetrical or asymmetrical.

Figure 3:
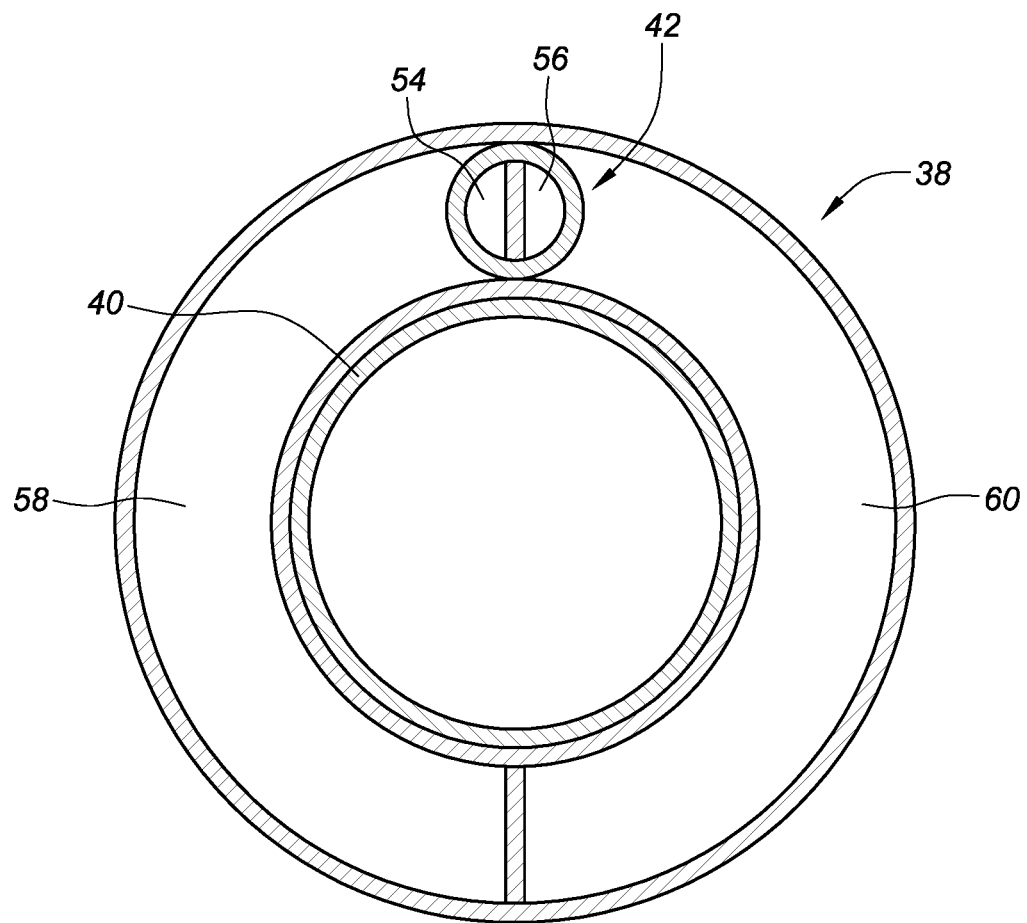
FIG. 3 is a cross-sectional view of the supply lumen for the movable manifold of FIGS. 2A-B, consistent with embodiments in the present disclosure.

FIG. 3 is a cross-sectional view of the supply lumen and the movable manifold of FIGS. 2A-B, consistent with embodiments in the present disclosure. The supply lumen 42 can include the first supply lumen portion 54 and the second supply lumen portion 56 to deliver fluid/gas to separate portions of the movable manifold 38. As shown in FIG. 3, the movable manifold 38 can be divided into two portions, where the first supply lumen portion is in fluid communication with a first movable manifold portion 58 and the second supply lumen portion 56 is in fluid communication with a second movable manifold portion 60. The movable manifold 38 is slideably coupled with the central lumen 40. This configuration allows for fluid/gas to be separately supplied (e.g., circulated by a pump (e.g., as part of the energy/fluid supply 16 of FIG. 1)) to each portion of the movable manifold 38. In other embodiments (not shown), multiple supply lumens (e.g., two supply lumens, three supply lumens, etc.) can be used instead of a single supply lumen with different portions as shown in FIG. 3.

One or more pumps can be used to control the circulation of the fluid/gas. For example, a first pump can circulate fluid through the first supply lumen portion 54 and the first portion of the movable manifold 38 and a second pump can supply fluid through the second supply lumen portion 56 and the second portion of the movable manifold 38. A pump (e.g., as part of the energy/fluid supply 16 of FIG. 1 or a separate pump (not shown)) can circulate a fluid/gas through, for example, the supply lumen 42, the movable manifold 38, and the balloon 36. The pump can also circulate the fluid/gas through other elements of the system 10 of FIG. 1 (e.g., a portion of the shaft 32 and/or the handle 20 of FIG. 1, etc.). Multiple pumps can be used to control circulation of a fluid.

In the embodiment shown in FIG. 3, the movable manifold 38 is separated into two portions by longitudinally dividing the movable manifold into the first movable manifold portion 58 (e.g., the left half of the movable manifold 38 cross-section in FIG. 3) and the second movable manifold portion 60 (e.g., the right half of the movable manifold 38 cross-section in FIG. 3). In another embodiment (not shown), the movable manifold can be divided into two portions creating a proximal movable manifold portion and a distal movable manifold portion (e.g., radially dividing the movable manifold 38).

In another embodiment (not shown), the first movable manifold portions 58 and the second movable manifold portion 60 can be separated into different portions. For example, the first movable manifold portion 58 and the second manifold portion 60 can each have a proximal portion and a distal portion. The supply lumen can be correspondingly coupled (e.g., in fluid communication) with the various portions of the movable manifold 38 to provide the fluid/gas to individual portions to allow for separate control/application of the specific portion as described herein. In other embodiments, the movable manifold can include multiple portions (e.g., a third movable manifold portion, a fourth movable manifold portion, etc.) where the supply lumen includes additional divisions to allow for individual control of the additional movable manifold portions.

In some embodiments (not shown), a movable manifold 38 can be divided such that separate supplies of fluid/gas can distribute the fluid/gas to various openings in the movable manifold 38 (e.g., three supply manifold portions to three separate portions of the movable manifold, four supply manifold portions to four separate portions of the movable manifold, etc.). In another embodiment, the supply lumen can have a path for fluid flow and supply the entire movable manifold 38 (not shown).

Figure 4A:
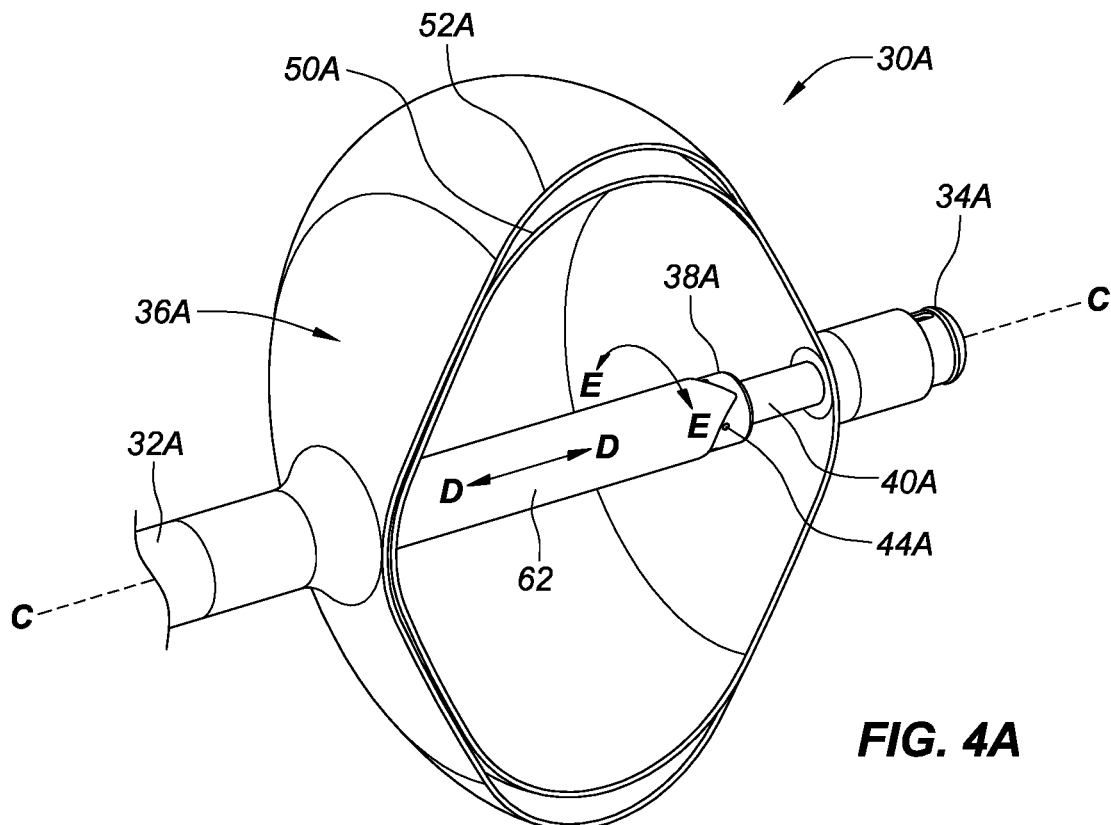
FIG. 4A is a partial fragmentary view of a distal end of an elongate medical device coupled with a balloon apparatus with a manifold and a movable opening cover, consistent with embodiments in the present disclosure.

FIG. 4A is a partial fragmentary view of a distal end of an elongate medical device coupled with a balloon apparatus with a manifold and a movable opening cover, consistent with embodiments in the present disclosure. The elongate medical device 32A can include a balloon apparatus 30A that includes a balloon 36A, and a central lumen 40A, where the central lumen 40A is inside the balloon 36A. A movable opening cover 62 (i.e., a movable manifold cover, a distribution apex, a distribution control element) can be slideably and rotatably coupled with the central lumen 40A. The central lumen 40A can include openings 44A (e.g., ports). The movable opening cover 62 can slide longitudinally (e.g., proximally and/or distally as indicated by an arrow D-D) and rotate about a longitudinal axis of the central lumen 40A (e.g., clockwise and counterclockwise as indicated by an arrow E-E) to cover a portion of the movable manifold 38A. The elongate medical device 32A and the balloon apparatus 30A can share a longitudinal axis defined by the line C-C.

As the movable opening cover 62 is moved (e.g., rotated as indicated by the arrow E-E and/or translated longitudinally as indicated by the arrow D-D), it can cover one or more of the openings 44A in the movable manifold 38A slideably coupled with the central lumen 40A. A shape of the movable opening cover 62 can include a triangular shape and/or an apex, that facilitates covering one or more of the openings 44A of the movable manifold 38A. In some configurations, the movable opening cover 62 can cover at least half of the openings 44A. Covering half of the openings 44A can allow for selected directionality of the flow of fluid/gas into the balloon 36A. In other embodiments, the movable manifold cover 62 can cover a portion of an opening 44A. This directionality can allow for protection and/or isolation of various portions of tissue and adjacent biological features. For example, when the balloon apparatus 30 is positioned proximate the PV, the phrenic nerve can be protected by moving the movable opening cover 62 into a first position that blocks a first set of openings (e.g., one or more openings) on the movable lumen 38A that would prevent the coolant/gas from being directed towards tissue proximate the phrenic nerve.

The movable opening cover 62 can be moved to a second position to cover a second set of openings (e.g., one or more openings where at least one opening is not part of the first set of openings) as needed. The need to move the movable opening cover 62 to the second position can be determined by any suitable method, including monitoring and/or sensors (e.g., diaphragm monitoring, temperature sensors, pacing catheters (e.g., phrenic pacing catheters), thermal probes (e.g., thermal probes) attached to the elongate medical device 32A, the central lumen 40A, the movable opening cover 62, the balloon 36A, or other suitable locations of the balloon apparatus or another device.

Position stops (not shown) can be used to set the location of the movable opening cover 62 to aid is positioning the movable opening cover 62 in a desired position with regards to the first position and the second position. For example, a first position stop can be used to set the movable opening cover 62 to the first opening and a second position stop can be used to set the movable opening cover 62 to cover the second opening. Additional position stops can be used depending in the number of openings 44A to be covered. The position stops can be, for example, mechanical (e.g., features or elements on one or more of the movable opening cover 62, the central lumen 40A, and/or the movable manifold 38A) or electromechanical (e.g., sensors).

The movable opening cover 62 can be made from any suitable material including a polymer (e.g., polyimide). The movable opening cover 62 can have various shapes/configurations to allow for different combinations of coverage of the openings 44A on the movable manifold 38A. In the embodiment shown in FIG. 4A, the movable opening cover 62 has a triangular portion to allow for covering one of the openings 44A. The shape of the movable opening cover 62 also allows for two or more (e.g., 10%, 20%, 25%, 30%, 33%, 40%, 50%, 60%, 66%, etc.) of the openings 44A to be covered. When the openings 44A are covered by the movable opening cover, the flow of fluid/gas through that blocked opening 44A is interrupted/stopped. This allows for control of the directionality of the flow of fluid/gas into the balloon 36A.

In addition to the movable opening cover 62 being movable longitudinally and rotationally, the movable manifold 38A can also be movable as described herein (e.g., see the movable manifold 38 in FIGS. 2A-B and related description). In this embodiment, the movable manifold 38A can be moved independently of the movable opening cover 62. For example, the movable manifold 38A can be translated longitudinally and/or rotated about the longitudinal axis of the central lumen 40A and the movable opening cover 62 can separately be translated longitudinally and/or rotated about the longitudinal axis of the central lumen 40A. The manifold and the movable opening cover can have separate mechanisms (e.g., separate pull/activation wires, control elements, knobs, levels, handles, etc.) for controlling movement from a proximal location of the elongate medical device (e.g., at the handle 20 of FIG. 1) or the control mechanisms can be combined (e.g., the longitudinal movement of the movable opening cover 62 and the movable manifold 38A can be coordinated/coupled).

The openings 44A can be located at various locations along the movable manifold 38A. For example, the openings 44A can be at a location that is proximate a manifold distal end (e.g., the manifold distal end 48 of FIGS. 2A-B). In some embodiments, the openings 44A can be located alternatively and/or additionally at a location between a manifold proximal end (e.g., the manifold proximal end 46 of FIGS. 2A-B) and the manifold distal end. The openings 44A can vary in different ways (e.g., location, number, size, shape, etc.) to allow for variation in treatment of the fluid such as different directions, angles, flow patterns, flow rates, etc. In some embodiments, the openings 44A can include, for example, a nozzle, orifice, or other suitable element to control and/or direct the flow of the fluid as it out of the movable manifold 38A and into the balloon 36A. For example, the nozzle, orifice, or other element can be a separate element or integral to the movable manifold 38A.

The central lumen 40A can provide fluid, medical devices that include any suitable sensor, wire (e.g., a guide wire), device, and/or other items commonly used in elongate medical device procedures. For example, the central lumen 40A can include a central opening, a hollow tube, and/or a tubular port. In some embodiments, the central lumen 40A can include more than one separate lumen which could include a lumen offset from the center of and/or separate the central lumen 40A.

The balloon 36A can be configured to occlude an opening in a body (e.g., a pulmonary vein in the heart or other opening in the body). When the balloon 36A is occluding the opening, a portion of the balloon 36A is in contact with tissue (e.g., a therapy site). The portion of the balloon 36A in contact with the tissue can facilitate therapy of the tissue (e.g., the creation of ablation lesions in, for example, the pulmonary vein (PV) or other locations in the body).

Similar to the description above for FIGS. 2A-B, the movable manifold 38A can be made from any suitable material (e.g., a metal, polymer, etc.) and can be coupled with, for example, the central lumen. The movable manifold 38A can be in any suitable configuration regarding a longitudinal length and wall thicknesses of the movable manifold 38A.

The contents of the balloon 36A (e.g., a fluid or a gas) can be cooled by any suitable means including, expansion of a liquid to a gas. The fluid/gas can then lower the temperature of the balloon 36A and then the tissue adjacent the balloon 36A. Specific portions of the balloon 36A can be targeted (or blocked) as described herein for therapy (or protection from therapy) to specific tissue portions.

In some embodiments (not shown), the central lumen 40A can be coupled with a manifold that is not movable (a fixed manifold). Similar to the embodiments described herein, the fixed manifold can include openings 44A in various patterns and arrangements. The movable opening cover 62 can be moved longitudinally and/or rotated to cover various openings 44A to block the flow of the fluid/gas.

The embodiments described herein can be applied to other balloon structures. For example, U.S. Pat. No. 8,052,680, issued on 8 Nov. 2011, and assigned to St. Jude Medical, Atrial Fibrillation Division, Inc. (the '680 patent), includes processes and devices for the treatment of atrial arrhythmia. A catheter and an introducer similar to embodiments described herein could be used with a balloon described in the '680 patent. The '680 patent is hereby incorporated by reference in its entirety as though fully set forth herein.

Figure 4B:
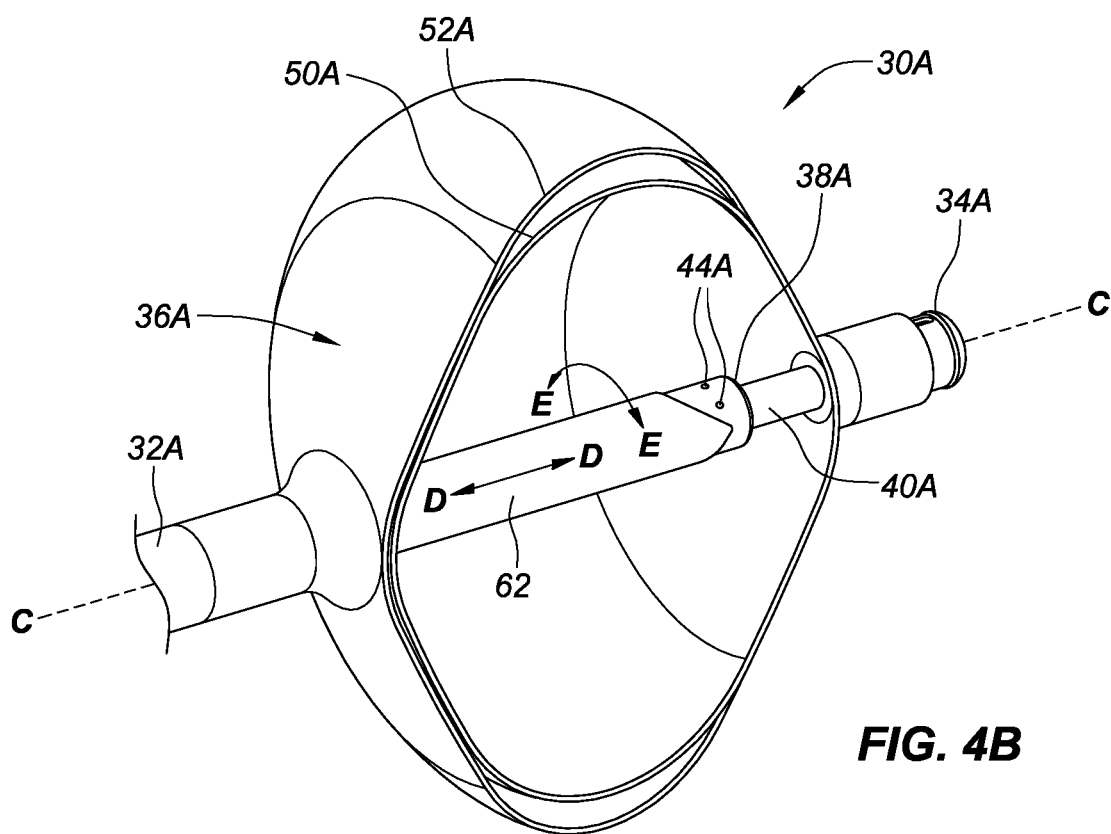
FIG. 4B is a partial fragmentary view of the distal end of the elongate medical device coupled with the balloon with the movable manifold and the port block tube of FIG. 4A, where the movable opening cover is rotated to block a second opening, consistent with embodiments in the present disclosure.

FIG. 4B is a partial fragmentary view of the distal end of the elongate medical device coupled with the balloon with the movable manifold and the port block tube of FIG. 4A, where the movable opening cover is rotated to block a second opening, consistent with embodiments in the present disclosure. The balloon apparatus 30A can include the elongate medical device 32A, which can include the balloon 36A coupled to the distal end portion of the elongate medical device 32A, where the balloon 36A can include a movable manifold 38A and a central lumen 40A. The movable manifold 38A can include a movable manifold proximal end (e.g., proximal end 46 in FIGS. 2A-B) and a movable manifold distal end (e.g., distal end 48 in FIGS. 2A-B), with the openings 44A on the movable manifold 38A In the embodiment of FIG. 4B, the openings 44A are shown being proximate the movable manifold distal end. In other embodiments the openings 44 can be located at any suitable location between the movable manifold proximal end and/or the movable manifold distal end. In still further embodiments, additional openings 44A can be located at various locations along the movable manifold 38A between the movable manifold proximal end and the movable manifold distal end. The additional openings 44A can allow for variations in the flow of the fluid as it flows from the movable manifold 38A into the balloon 36A.

Figure 5:
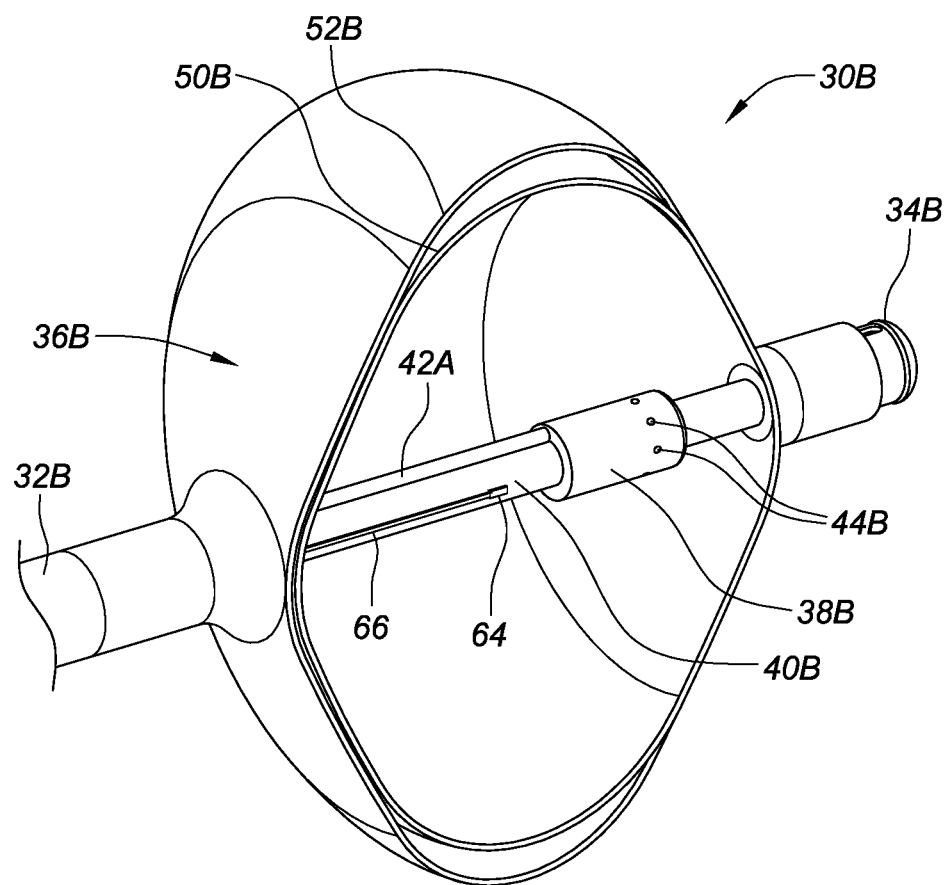
FIG. 5 is a partial fragmentary view of a distal end of an elongate medical device with a balloon with a movable manifold and a pressure sensor, consistent with embodiments in the present disclosure.

FIG. 5 is a partial fragmentary view of a distal end of an elongate medical device with a balloon with a movable manifold and a pressure sensor, consistent with embodiments in the present disclosure. FIG. 5A shows an exemplary configuration of an elongate medical device 32B a central lumen 40B, a supply lumen 42A, and a movable manifold 38B (similar to the elongate medical device 32 shown in FIGS. 2A-B and described above) plus a pressure sensor 64. As described herein, the supply lumen 42A can be used to supply a fluid to the balloon 36B through the movable manifold 38B. The central lumen 40B can also be used with, for example, a guide wire to maneuver the elongate medical device 32B to a location in the body 14 (FIG. 1). The pressure sensor 64 can be, for example, a MEMS sensor that can determine a pressure inside the balloon 36B. The pressure inside the balloon 36B can vary during therapy. In some instances, a leak or a problem with the rate of flow (e.g., a kink in a line from the fluid supply 16 of FIG. 1) of a gas/fluid into the balloon 36B can be indicated by data provided by the pressure sensor 64 (e.g., maximum and/or minimum pressure, rate of change of pressure, etc.).

For example, if the pressure determined by the pressure sensor 64 rapidly increases, this could represent a failure of a part of the balloon apparatus 30B, which could lead to the balloon 36B overfilling with the fluid/gas which could lead to balloon failure. The data from the pressure sensor 64 could allow a user or an automated control system (e.g., an electronic control unit that can be part of the energy/fluid supply 16 of FIG. 1) to turn off the flow of gas/fluid into the balloon 36B to prevent failure of the balloon 36B. As shown in FIG. 5A, the pressure sensor 64 can be electrically connected by a wire 66 to, for example, the energy/fluid supply 16 of FIG. 1 and/or an electronic control unit.

The pressure sensor 64 can be coupled with the central lumen 40B at any suitable location inside the balloon 36B. The pressure sensor 64 can be positioned to permit movement of the movable manifold 38B. For example, the pressure sensor 64 can be embedded into an outer wall surface of the central lumen 40B (e.g., the pressure sensor 64 is flush with the outer wall of the central lumen 40B). In another embodiment (not shown), if the pressure sensor 64 is not flush with the outer wall of the central lumen 40B, the movable manifold can be configured to pass over the pressure sensor while moving longitudinally along the central lumen 40B.

As discussed above, the pressure sensor 64 can be electrically connected by a wire 66 to, for example, the energy/fluid supply 16 of FIG. 1 and/or an electronic control unit. The pressure sensor 64 can be any suitable type of pressure sensor, including a MEMS sensor, a fiber optic sensor, a strain gauge, or other sensors that can determine a pressure inside the balloon 36B. The pressure inside the balloon 36B can vary during therapy and the pressure sensor 64 can provide feedback regarding changes in the pressure of the fluid/gas inside the balloon 36B (e.g., monitor the increase in pressure as the fluid/gas is added to the balloon 36B, monitor for decreases in pressure that may be caused by leaks or other issues, etc.).

The elongate medical device 32 can be connected with, for example, a processor and a memory storing non-transitory computer-readable instructions, as discussed herein (e.g., as part of the ECU, or a separate processor and a separate memory, or a combination of the two). The ECU may be programmed with a computer program (e.g., software) encoded on a computer-readable storage medium for assessing the pressure inside the balloon 36B and changes to the pressure. The instructions can be executable to compute, for example, the rates of change of pressure in the balloon 36B, limits on maximum and minimum pressure in the balloon 36B, flow rates of the fluid/gas into (and out of the balloon 36B, and/or other related characteristics.

It should be understood that the system (e.g., system 10 of FIG. 1) may include a conventional processing apparatus known in the art, capable of executing pre-programmed instructions stored in an associated memory, all performing in accordance with the functionality described herein. It is contemplated that the methods described herein, including without limitation the method steps of embodiments of the disclosure, will be programmed in a preferred embodiment, with the resulting software being stored in an associated memory and where so described, may also constitute the means for performing such methods. Implementation of the embodiments, in software, in view of the foregoing enabling description, would require no more than routine application of programming skills by one of ordinary skill in the art. Such a system may further be of the type having both ROM and RAM, a combination of non-volatile and volatile (modifiable) memory so that the software can be stored and yet allow storage and processing of dynamically produced data and/or signals.

Additional information and examples can be found in U.S. application No. 62/506,853, filed on May 16, 2017, U.S. application No. 62/578,352, filed on Oct. 27, 2017, U.S. application No. 62/578,320, filed on Oct. 27, 2017, and U.S. application No. 62/578,325, filed on Oct. 27, 2017, each of which is hereby incorporated by reference as if set forth fully herein.

Although at least one embodiment of a cryo-therapy balloon has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for providing therapy to heart tissue, comprising:
    a balloon;
    a movable manifold comprising a first portion comprising a first plurality of openings and a second portion comprising a second plurality of openings, the movable manifold located inside the balloon and the movable manifold configured to distribute a fluid within the balloon, wherein the movable manifold is divided along a longitudinal axis of the movable manifold to create the first portion and the second portion of the movable manifold, wherein the first plurality of openings distribute the fluid at a first flow rate and the second plurality openings distribute the fluid at a second flow rate, wherein the first flow rate and the second flow rate are different;
    an elongate shaft comprising a proximal end and a distal end, the distal end of the elongate shaft being coupled with the balloon;
    a central lumen, wherein the movable manifold is movably coupled with the central lumen; and
    a supply lumen comprising a proximal end and a distal end, the supply lumen comprising a first portion in fluid communication with the first portion of the movable manifold and a second portion in fluid communication with the second portion of the movable manifold, wherein the supply lumen is divided along a longitudinal axis of the supply lumen to create the first portion and the second portion of the supply lumen, and wherein the supply lumen is longitudinally movable.

2. The medical device of claim 1, wherein the balloon comprises a plurality of layers and is configured to be filled with a cryogenic substance.

3. The medical device of claim 1, wherein the first plurality of openings are circumferentially spaced around the first portion of the movable manifold and the second plurality of openings are circumferentially spaced around the second portion of the movable manifold.

4. The medical device of claim 1, wherein the supply lumen is configured to be moved longitudinally by a user interacting with a proximal end portion of the supply lumen.

5. The medical device of claim 1, further comprising a fluid supply that circulates a fluid through the supply lumen, the medical device, the movable manifold, and the balloon.

6. The medical device of claim 1, wherein the supply lumen is adjacent to the central lumen.

7. A system, comprising:
    a medical device according to claim 1,
    wherein an outer portion of the supply lumen is surrounded by the balloon and the outer portion of the supply lumen that is surrounded by the balloon comprises an outlet at a distal end of the supply lumen and an inlet at a proximal end of the supply lumen; and
    a fluid supply that circulates a fluid through the lumen, the medical device, the movable manifold, and the balloon.

8. The medical device of claim 1, further comprising a pressure sensor, wherein the pressure sensor is coupled with the central lumen.

9. The medical device of claim 8, wherein the pressure sensor is selected from the group consisting of a MEMS pressure sensor, a fiber optic sensor, and a strain gauge.

10. The medical device of claim 8, further comprising an electronic control unit configured to control circulation of the fluid and monitor, using the pressure sensor, a pressure inside the balloon.

11. A system, comprising:
    a medical device according to claim 1,
    a first pump; and
    a second pump,
    wherein the first pump is configured to circulate fluid through the first supply lumen and the second pump is configured to circulate fluid through the second supply lumen.

12. A medical therapy apparatus, comprising:
    a balloon, positioned at a distal end portion of an elongate structure;
    a central lumen coupled with the balloon;
    a manifold comprising a plurality of ports circumferentially spaced about the manifold, the plurality of ports in fluid communication with an interior of the balloon, wherein the manifold is coupled with the central lumen; and
    a movable manifold cover, the moveable manifold cover comprising a triangular portion, wherein the movable manifold cover is configured to slide longitudinally and rotate about a longitudinal axis of the central lumen, wherein the triangular portion is configured to cover one or more of the plurality of ports and to block the fluid communication between the manifold and the interior of the balloon and wherein the triangular portion is configured to cover any one port of the plurality of ports when at a first longitudinal position and the triangular portion is configured to cover any two adjacent ports of the plurality of ports when at a second longitudinal position.

13. The balloon therapy apparatus of claim 12, wherein the manifold is movable longitudinally along the central lumen.

14. The balloon therapy apparatus of claim 12, wherein the central lumen comprises a pressure sensor coupled with an outer surface of the central lumen and configured to detect a pressure within the balloon.

15. The balloon therapy apparatus of claim 12, wherein the manifold is coupled with an exterior surface of central lumen.

16. A medical device, comprising:
    a balloon, positioned at a distal end portion of an elongate structure;
    a central lumen coupled with the balloon;
    a movable manifold comprising a plurality of distribution elements, wherein the manifold is coupled with the central lumen; and
    a distribution control element movably coupled to the movable manifold, wherein the distribution control element is configured to slide longitudinally and rotate about a longitudinal axis of the central lumen, wherein the distribution control element comprises a triangular portion, wherein the triangular portion is configured to cover any one distribution element of the plurality of distribution elements when at a first longitudinal position and the triangular portion is configured to cover any two distribution elements of the plurality of distribution elements when at a second longitudinal position.

17. The medical device of claim 16, wherein the distribution element comprises one or more openings.

18. The medical device of claim 17, wherein the distribution control element is configured to selectively cover a portion of one or more of the one or more openings.

* * * * *